(12) United States Patent
Cook et al.

(10) Patent No.: US 8,690,956 B2
(45) Date of Patent: *Apr. 8, 2014

(54) TALAR IMPLANTS AND METHODS OF USE

(75) Inventors: Stephen D. Cook, New Orleans, LA (US); Shoib Bajaj, Kenner, LA (US); Peter Strzepa, Austin, TX (US)

(73) Assignee: Fellowship of Orthopaedic Researchers, Inc., Metairie, LA (US)

( * ) Notice: Subject to any disclaimer, the term of this patent is extended or adjusted under 35 U.S.C. 154(b) by 26 days.

This patent is subject to a terminal disclaimer.

(21) Appl. No.: 13/207,554

(22) Filed: Aug. 11, 2011

(65) Prior Publication Data

US 2012/0046753 A1     Feb. 23, 2012

Related U.S. Application Data

(60) Provisional application No. 61/376,076, filed on Aug. 23, 2010.

(51) Int. Cl.
*A61F 2/66*     (2006.01)

(52) U.S. Cl.
USPC .................................. 623/21.18; 623/14.12

(58) Field of Classification Search
USPC ........................................ 623/14.12, 21.18
See application file for complete search history.

(56) References Cited

U.S. PATENT DOCUMENTS

| | | | |
|---|---|---|---|
| 4,021,864 | A | 5/1977 | Waugh |
| 4,158,894 | A | 6/1979 | Worrell |
| 4,231,121 | A | 11/1980 | Lewis |
| 4,281,419 | A | 8/1981 | Treace |
| 4,488,843 | A | 12/1984 | Achille |
| 4,849,692 | A | 7/1989 | Blood |
| 4,919,667 | A | 4/1990 | Richmond |
| 4,945,305 | A | 7/1990 | Blood |
| 4,964,867 | A | 10/1990 | Boger |
| 5,019,104 | A | 5/1991 | Whiteside et al. |
| 5,092,896 | A | 3/1992 | Meuli et al. |
| 5,236,462 | A | 8/1993 | Mikhail |

(Continued)

FOREIGN PATENT DOCUMENTS

| CA | 2232068 | 3/1997 |
|---|---|---|
| DE | 69732500 T2 | 7/2006 |

(Continued)

OTHER PUBLICATIONS

U.S. Patent and Trademark Office, Non-Final Office Action Issued Against U.S. Appl. No. 12/074,770; Nov. 24, 2010; 14 pages.

(Continued)

*Primary Examiner* — David Isabella
*Assistant Examiner* — Randy Shay
(74) *Attorney, Agent, or Firm* — Frommer Lawrence & Haug LLP

(57) ABSTRACT

Implant devices, and method of using the same, are provided. The implant devices have a head and a stem. The head has an upper surface, a perimeter surface, and a lower surface. The upper surface is blended into the perimeter surface. The perimeter surface is blended into the lower surface. The upper surface has a general shape of at least a portion of a superior articular surface of a talus and at least a portion of a medial articular surface of a talus. The stem has a cylindrical portion, which optionally has at least one circumferential groove.

20 Claims, 4 Drawing Sheets

(56) References Cited

U.S. PATENT DOCUMENTS

| | | | |
|---|---|---|---|
| 5,246,460 A | 9/1993 | Goodfellow et al. | |
| 5,253,987 A | 10/1993 | Harrison | |
| 5,263,987 A | 11/1993 | Shah | |
| 5,306,311 A | 4/1994 | Stone | |
| 5,358,525 A | 10/1994 | Fox | |
| 5,383,937 A | 1/1995 | Mikhail | |
| 5,580,353 A | 12/1996 | Mendes et al. | |
| 5,600,330 A | 2/1997 | Blood | |
| 5,609,640 A | 3/1997 | Johnson | |
| 5,645,605 A | 7/1997 | Klawitter | |
| 5,683,466 A | 11/1997 | Vitale | |
| 5,742,394 A | 4/1998 | Hansen | |
| 5,744,953 A | 4/1998 | Hansen | |
| 5,749,874 A | 5/1998 | Schwartz | |
| 5,766,259 A | 6/1998 | Sammarco | |
| 5,767,669 A | 6/1998 | Hansen et al. | |
| 5,767,960 A | 6/1998 | Orman et al. | |
| 5,782,835 A | 7/1998 | Hart | |
| 5,782,927 A | 7/1998 | Klawitter et al. | |
| 5,824,095 A | 10/1998 | Di Maio et al. | |
| 5,831,260 A | 11/1998 | Hansen | |
| 5,953,683 A | 9/1999 | Hansen et al. | |
| 6,159,247 A | 12/2000 | Klawitter et al. | |
| 6,172,499 B1 | 1/2001 | Ashe | |
| 6,183,519 B1 | 2/2001 | Bonnin et al. | |
| 6,217,616 B1 | 4/2001 | Ogilvie | |
| 6,246,231 B1 | 6/2001 | Ashe | |
| 6,251,143 B1 | 6/2001 | Schwartz et al. | |
| 6,417,839 B1 | 7/2002 | Odell | |
| 6,436,146 B1 | 8/2002 | Hassler et al. | |
| 6,473,167 B1 | 10/2002 | Odell | |
| 6,528,991 B2 | 3/2003 | Ashe | |
| 6,575,986 B2 | 6/2003 | Overaker | |
| 6,610,067 B2 | 8/2003 | Tallarida et al. | |
| 6,626,945 B2 | 9/2003 | Simon | |
| 6,626,950 B2 | 9/2003 | Brown | |
| 6,663,669 B1 | 12/2003 | Reiley | |
| 6,679,917 B2 | 1/2004 | Ek | |
| 6,699,292 B2 | 3/2004 | Ogilvie et al. | |
| 6,709,460 B2 | 3/2004 | Merchant | |
| D490,900 S | 6/2004 | Ogilvie et al. | |
| 6,754,596 B2 | 6/2004 | Ashe | |
| 6,784,660 B2 | 8/2004 | Ashe | |
| 6,797,006 B2 | 9/2004 | Hodorek | |
| 6,814,757 B2 | 11/2004 | Kopylov et al. | |
| 6,815,651 B2 | 11/2004 | Odell | |
| 6,854,972 B1 | 2/2005 | Elian | |
| 6,856,823 B2 | 2/2005 | Ashe | |
| 7,027,634 B2 | 4/2006 | Odell | |
| 7,106,431 B2 | 9/2006 | Odell | |
| 7,161,686 B2 | 1/2007 | Duling et al. | |
| 7,204,854 B2 | 4/2007 | Guederian et al. | |
| 7,264,634 B2 | 9/2007 | Schmieding | |
| 7,314,488 B2 | 1/2008 | Reiley | |
| 7,618,451 B2 | 11/2009 | Berez et al. | |
| 8,012,217 B2 * | 9/2011 | Strzepa et al. | 623/21.18 |
| 2003/0135280 A1 | 7/2003 | Kopylov et al. | |
| 2003/0233149 A1 | 12/2003 | Hodorek | |
| 2004/0039447 A1 | 2/2004 | Simon et al. | |
| 2004/0230303 A1 | 11/2004 | Gomes et al. | |
| 2004/0230315 A1 | 11/2004 | Ek | |
| 2005/0033426 A1 | 2/2005 | Ogilvie et al. | |
| 2005/0084513 A1 | 4/2005 | Tang | |
| 2005/0137708 A1 | 6/2005 | Clark | |
| 2005/0137713 A1 | 6/2005 | Bertram | |
| 2006/0069446 A1 | 3/2006 | Ragusa et al. | |
| 2006/0190002 A1 | 8/2006 | Tallarida et al. | |
| 2006/0229726 A1 * | 10/2006 | Ek | 623/17.11 |
| 2006/0241778 A1 | 10/2006 | Ogilvie | |
| 2007/0005143 A1 | 1/2007 | Ek et al. | |
| 2007/0032876 A1 | 2/2007 | Clark | |
| 2007/0078334 A1 | 4/2007 | Scully et al. | |
| 2007/0123993 A1 | 5/2007 | Hassler et al. | |
| 2007/0198095 A1 | 8/2007 | Vander Meulen et al. | |
| 2007/0225820 A1 | 9/2007 | Thomas et al. | |
| 2007/0250169 A1 | 10/2007 | Lang | |
| 2008/0188942 A1 | 8/2008 | Brown et al. | |
| 2009/0228104 A1 | 9/2009 | Strzepa et al. | |
| 2009/0228106 A1 | 9/2009 | Strzepa et al. | |
| 2009/0240336 A1 | 9/2009 | Vander Meulen et al. | |
| 2010/0004743 A1 * | 1/2010 | Strzepa et al. | 623/14.12 |
| 2010/0121451 A1 | 5/2010 | Strzepa et al. | |
| 2010/0121452 A1 | 5/2010 | Strzepa et al. | |

FOREIGN PATENT DOCUMENTS

| | | |
|---|---|---|
| DE | 602004003510 T2 | 8/2007 |
| DE | 60126129 T2 | 11/2007 |
| EP | 1112753 A1 | 2/2001 |
| EP | 1437104 A1 | 7/2004 |
| EP | 1955676 A1 | 8/2008 |
| ES | 2141533 | 3/2000 |
| JP | 2004202233 A | 7/2004 |
| WO | WO 8802844 | 4/1988 |
| WO | WO 9012276 | 10/1990 |
| WO | WO 9203117 | 3/1992 |
| WO | WO 9409280 | 4/1994 |
| WO | WO 9602008 | 1/1996 |
| WO | WO 9710780 | 3/1997 |
| WO | WO 9819637 | 5/1998 |
| WO | WO 0013617 | 3/2000 |
| WO | WO 0133162 A1 | 5/2001 |
| WO | WO 0170138 A1 | 9/2001 |
| WO | WO 2004093767 A1 | 11/2001 |
| WO | WO 0243627 A1 | 6/2002 |
| WO | WO 2007041678 | 4/2007 |
| WO | WO 2007041678 A2 | 4/2007 |
| WO | WO 2007059459 A2 | 5/2007 |
| WO | WO 2007103362 A2 | 9/2007 |
| WO | WO 2007109752 A2 | 9/2007 |
| WO | WO 2009111624 A2 | 9/2009 |
| WO | WO 2010003015 | 1/2010 |

OTHER PUBLICATIONS

"Pyrocarbon-Information for Surgeons" downloaded from http://www.pyrocarbon.com/index.php on Feb. 12, 2008.

U.S. Patent and Trademark Office, Non-Final Office Action Issued Against U.S. Appl. No. 12/074,770; Oct. 28, 2009; 1-8 pages; U.S.A.

U.S. Patent and Trademark Office, Non-Final Office Action Issued Against U.S. Appl. No. 12/074,770; Dec. 28, 2009; 1-9 pages; U.S.A.

U.S. Patent and Trademark Office, Non-Final Office Action Issued Against U.S. Appl. No. 12/074,770; Apr. 27, 2010; 1-12 pages; U.S.A.

U.S. Patent and Trademark Office, Final Office Action Issued Against U.S. Appl. No. 12/074,770; Aug. 31, 2010; 1-12 pages; U.S.A.

U.S. Patent and Trademark Office, Non-Final Office Action Issued Against U.S. Appl. No. 12/687,672; Apr. 5, 2011; 11 pages; U.S.A.

U.S. Patent and Trademark Office, Non-Final Office Action Issued Agsint U.S. Appl. No. 12/687,702; Apr. 13, 2011; 7 pages; U.S.A.

U.S. Patent and Trademark Office, Non-Final Office Action Issued Agsint U.S. Appl. No. 12/396,872; Apr. 13, 2011; 7 pages; U.S.A.

U.S. Patent and Trademark Office, Non-Final Office Action Issued Agsint U.S. Appl. No. 12/396,872; Jul. 6, 2011; 18 pages; U.S.A.

U.S. Patent and Trademark Office; Final Office Action Issued in Against U.S. Appl. No. 12/074,770; May 11, 2011; 12 pages; U.S.A.

U.S. Patent and Trademark Office; Advisory Action Issued Against U.S. Appl. No. 12/074,770; Jun. 22, 2011; 3 pages; U.S.A.

European Patent Office, Office Action Issued Against European Application No. 09716338.0; Oct. 19, 2010; 2 pages; Europe.

U.S. Patent and Trademark Office; Notice of Allowance and Fee(s) Due, Issued in connection with U.S. Appl. No. 12/319,869; Jun. 24, 2011;13 pages; U.S.A.

U.S. Patent and Trademark Office; Non-Final Office Action, Issued in connection with U.S. Appl. No. 12/319,869; Nov. 29, 2010; 16 pages; U.S.A.

"Pyrocarbon in Orthopedics", downloaded from www.pyrocarbon.com/pyrocarbon-orthopedic-implants.php on Feb. 12, 2008, p. 1-4.

"Pyrolytic Carbon" downloaded from http://en.wikipedia.org/wiki/Pyrolytic_carbon on Feb. 12, 2008, p. 1-2.

(56) References Cited

OTHER PUBLICATIONS

Patent Cooperation Treaty, PCT International Search Report Issued in Connection with International Appliction No. PCT/US09/36159; May 13, 2009; 1-2 pages; Europe.

Patent Cooperation Treaty, PCT Written Opinion of the International Searching Authority Issued in Connection with International Appliction No. PCT/US09/36159; May 13, 2009; 1-9 pages; Europe.

Patent Cooperation Treaty, PCT International Search Report Issued in Connection with International Appliction No. PCT/US09/049441; Aug. 26, 2009; 1-2 pages; Europe.

Patent Cooperation Treaty, PCT Written Opinion of the International Searching Authority Issued in Connection with International Appliction No. PCT/US09/049441; Aug. 26, 2009; 1-6 pages; Europe.

Patent Cooperation Treaty, PCT International Search Report Issued in Connection with International Appliction No. PCT/US2010/046654; Nov. 29, 2010; 1-5 pages; Europe.

Patent Cooperation Treaty, PCT Written Opinion of the International Searching Authority Issued in Connection with International Appliction No. PCT/US2010/046654; Nov. 29, 2010; 1-8 pages; Europe.

U.S. Patent and Trademark Office; Non-Final Office Action, Issued Against U.S. Appl. No. 12/868,112; 7 pages; U.S.A., Apr. 26, 2012.

* cited by examiner

TALAR IMPLANTS AND METHODS OF USE

CROSS-REFERENCE TO RELATED APPLICATIONS

This patent application claims the priority and benefit of U.S. Provisional Patent Application No. 61/376,076 filed on Aug. 23, 2010.

FIELD OF THE INVENTION

This disclosure relates to devices and methods for the repair of articular cartilage defects. In particular embodiments of this disclosure relate to new and improved implants that serve as a replacement for diseased or damaged cartilage in joints such as human ankles, and in more particularity talar cartilage.

BACKGROUND OF THE INVENTION

Cartilage acts as a pad between bones to reduce friction and prevent the bones from grinding against one another. Over time, due to injury and/or heredity, however, lesions such as fissures, cracks or crazes can form in the cartilage. In some cases, osteochondral, the lesion penetrates to the subchondral surface of the bone. In other cases, chondral, the lesion does not penetrate to the subchondral surface of the bone.

One past approach for regenerating new cartilage has been autologous chondrocyte transplantation. Other techniques, aimed at repair instead of regeneration, have included debridement, lavage, microfracturing, drilling, and abrasion arthroplasty. These procedures generally involve penetrating the region of vascularization in the subchondral bone with an instrument until bleeding occurs. Formation of a fibrin clot differentiates into fibrocartilage, which then covers the defect site. A further alternative approach has been to undergo a total replacement of the joint.

SUMMARY OF THE INVENTION

Definitions

In various illustrating embodiments, the term "torus" means the surface of a toriod.

In various illustrating embodiments, the term "tubular radius" refers to the radius of the tube of a torus, as opposed to the "major radius," which refers to the radius from the center of the torus to the center of the tube.

In various illustrating embodiments, geometric terms such as "circle", "circular," "cylinder", "cylindrical," "cone," "conical," "normal," and the like are used as references and for clarity of understanding, as would be understood by one of ordinary skill in the art. Accordingly, these terms should not be limited to strict Euclidean standards.

Various illustrating embodiments of the present disclosure provide implant devices, preferably for use in human joints, including the human ankle and specifically the talus. In accordance with one aspect of an illustrating embodiment of the present disclosure an implant may be provided which includes a head and a stem. The head may be bounded by an upper surface, a perimeter surface, and a lower surface. The upper surface may be blended into the perimeter surface, and the perimeter surface may be blended into the lower surface. Preferably, the upper surface has the general shape of portions of the superior and medial articular surfaces of a talus, which may consist of the trochlea for the tibia, and the surface for the medial malleolus of the tibia. The stem may have a cylindrical portion, and optionally a truncated conical portion. The cylindrical portion may be affixed to and extend downward from the lower surface of the head. Optionally, the cylindrical portion may have at least one circumferential groove extending continuously around at least one stem circular perimeter.

In accordance with another aspect of an illustrating embodiment of the present invention, a method of repairing articular cartilage using the implant device may be provided. The method of this illustrative embodiment includes locating articular cartilage having a lesion. An implant device, as described above, may be selected preferably having dimensions compatible with the lesion. A hole may be formed through the cartilage and subchondral bone, into the cancellous bone. The implant device may be inserted into the hole so that the lower and perimeter surfaces of the head of the implant device abut against the prepared subchondral and cancellous bone and the stem of the implant device abuts against the prepared cancellous bone.

In the detailed description which follows in conjunction with the drawings, like parts are given like reference numerals, and the vertical, horizontal and depth orientations of a given embodiment are specified explicitly in at least one drawing of an illustrative embodiment.

BRIEF DESCRIPTION OF THE DRAWINGS

The drawing figures are not necessarily to scale and certain features of the implant devices may be shown exaggerated in scale or in somewhat schematic form in the interest of clarity and conciseness, wherein.

DISCLOSURE OF ALTERNATIVE EMBODIMENTS

Figure 1:
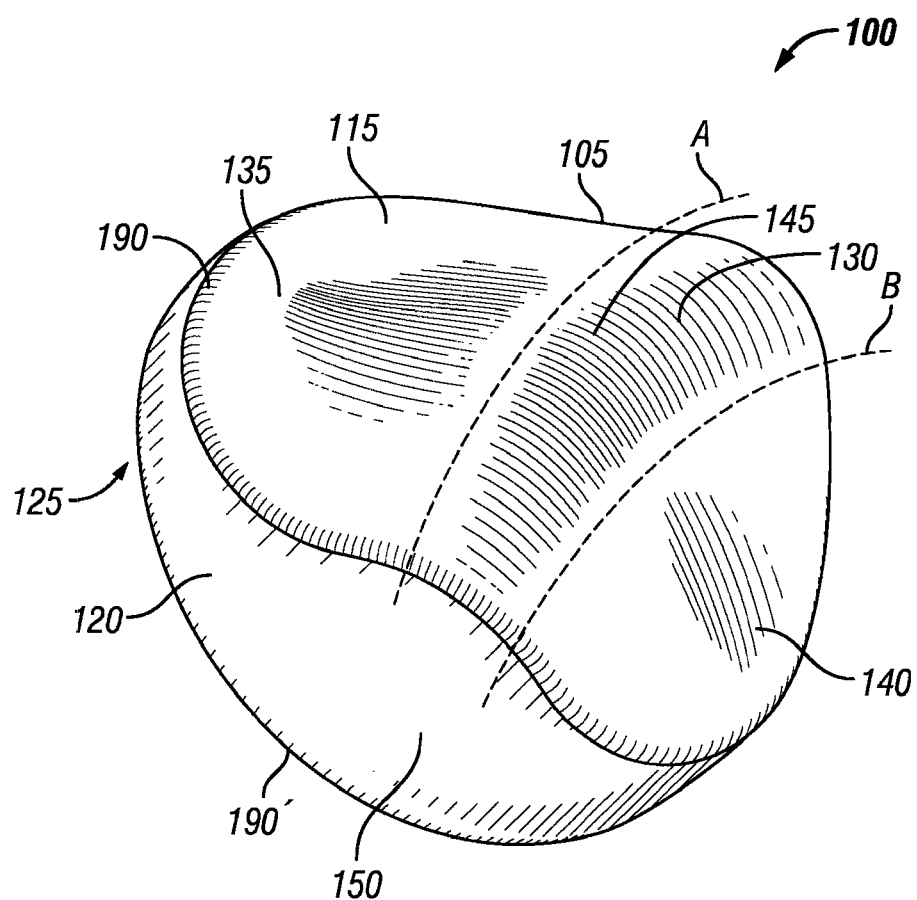
FIG. 1 is a top perspective view of one embodiment of an implant.

FIGS. 1-7 provide an illustrative embodiment of an implant 100, in which the vertical, V, horizontal, H, and depth, D, orientations of this embodiment are depicted in FIGS. 2-5. The implant 100 may be used to replace portions of the superior and medial articulating surfaces of the talus. The implant 100 may include a head 105 and a stem 110. The head 105 may be bound by three surfaces: an upper surface 115, a perimeter, side, or circular, surface 120, and a lower surface 125. The upper surface 115 may be blended at a first blend 190 into the perimeter surface 120. The perimeter surface 120 may be blended at a second blend 190' into the lower surface 125. All blends disclosed herein, unless otherwise noted, may each have an edge radius independently selected from a length ranging from about 0.1 millimeters to about 1 millimeter.

The upper surface 115 may be shaped to mimic portions of the superior and medial articular surfaces of a talus. For ease of reference, the upper surface 115 may be thought of as segmented into a first portion 130, a second portion 135, and a third portion 140. The first portion 130 may be tangent on its lateral edge to the medial edge of the second portion 135. The first portion 130 may also be tangent on its medial edge to the lateral edge of the third portion 140. In an embodiment, with reference to FIG. 1, the first portion 130 may be generally bounded on its lateral and medial edges by dashed lines A and B.

The first portion 130 may be a convex surface having a generally toroidal shape with a major radius ranging from about 9 millimeters to about 31 millimeters, alternatively from about 14 millimeters to about 26 millimeters, and alternatively about 16 millimeters. The minor (tubular) radius of the first portion 130 may range from about 2 millimeters to about 6 millimeters, alternatively from about 3 millimeters to about 5 millimeters, and alternatively about 4 millimeters. The first portion 130 may have an apex point 145 which may be the most superior point on the upper surface 115. In an embodiment, the apex point 145 may be the most superior point on the upper surface 115, may be located at the center of a cord of the outer, non-blended cylindrical portion 150 of the perimeter surface 120, and may be generally closer to the second portion 135 than the third portion 140. The second portion 135 may be a generally convex-concave shape having a toroidal saddle shape. The toroidal saddle shape of the second portion 135 may have a major radius in its plane of convex curvature ranging from about 20 millimeters to about 100 millimeters, alternatively from about 40 millimeters to about 80 millimeters, and alternatively about 60 millimeters. The toroidal saddle shape of the second portion 135 may have a minor (tubular) radius in its plane of concave curvature ranging from about 10 millimeters to about 70 millimeters, alternatively from about 25 millimeters to about 55 millimeters, and alternatively about 40 millimeters. The third portion 140 may have the general shape of a portion of the surface of a right circular cone with an aperture angle ranging from about 120 degrees to about 178 degrees, alternatively from about 140 degrees to about 160 degrees, and alternatively about 150 degrees.

In an embodiment, the lower surface 125 may be a generally flat, planer surface. In an embodiment, the normal of the flat, planer lower surface 125 may be directed downward from the horizontal at an angle ranging from about 15 degrees to about 75 degrees, alternatively from about 30 degrees to about 60 degrees, alternatively about 45 degrees.

The implant 100 may have an overall length ranging from about 10 millimeters to about 20 millimeters. Alternatively, the implant 100 may have an overall length of about 14 millimeters, alternatively about 15 millimeters, alternatively about 16.5 millimeters, alternatively about 17.5 millimeters. The stem 110 may have an overall length ranging from about 4 millimeters to about 8 millimeters. Alternatively, the stem 110 may have an overall length of about 6 millimeters.

In an embodiment, the perimeter surface 120 may be a generally cylindrical surface 150 that may have a diameter ranging from about 10 millimeters to about 30 millimeters, alternatively from about 12.5 millimeters to about 20 millimeters, alternatively the diameter of the cylindrical perimeter surface 120 may be about 12.5 millimeters, about 15 millimeters, about 17.5 millimeters, and about 20 millimeters. In an embodiment, at least a portion of the stem 110 may be a generally cylindrical surface 160 having a diameter ranging from about 5 millimeters to about 10 millimeters, alternatively from about 6 millimeters to about 8.5 millimeters, alternatively about 6 millimeters, and alternatively about 8.5 millimeters. In an embodiment, the stem cylindrical surface 160 may be blended in a third blend or a corner fillet 200 into the lower surface 125 of the head 105. In an embodiment, the stem cylindrical surface 160 may be blended in a fourth blend 190" into its base 175. In an embodiment, the head cylindrical perimeter surface 120 may be generally concentric with the stem cylindrical surface 160.

Figure 2:
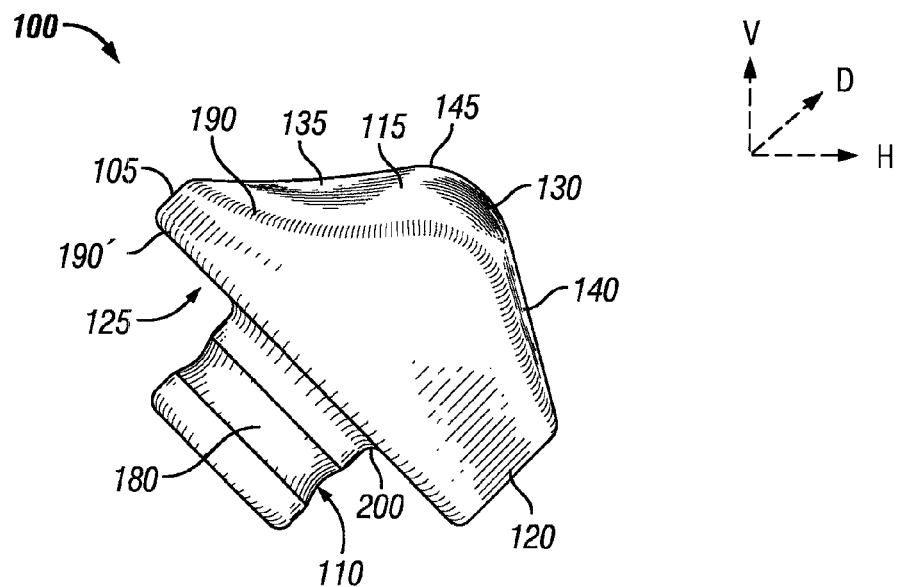
FIG. 2 is a first side view of the implant of FIG. 1.
Figure 3:
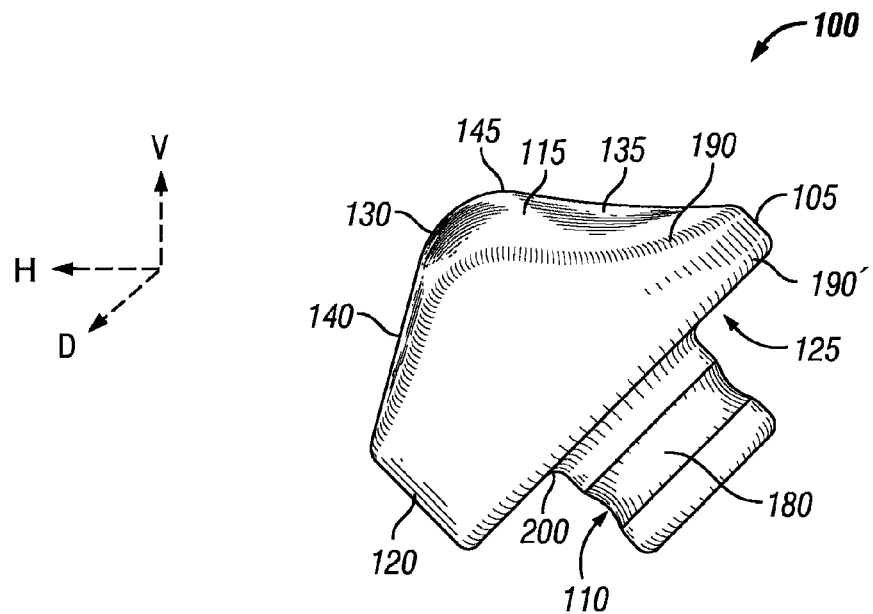
FIG. 3 is a second side view of the implant of FIG. 1.
Figure 4:
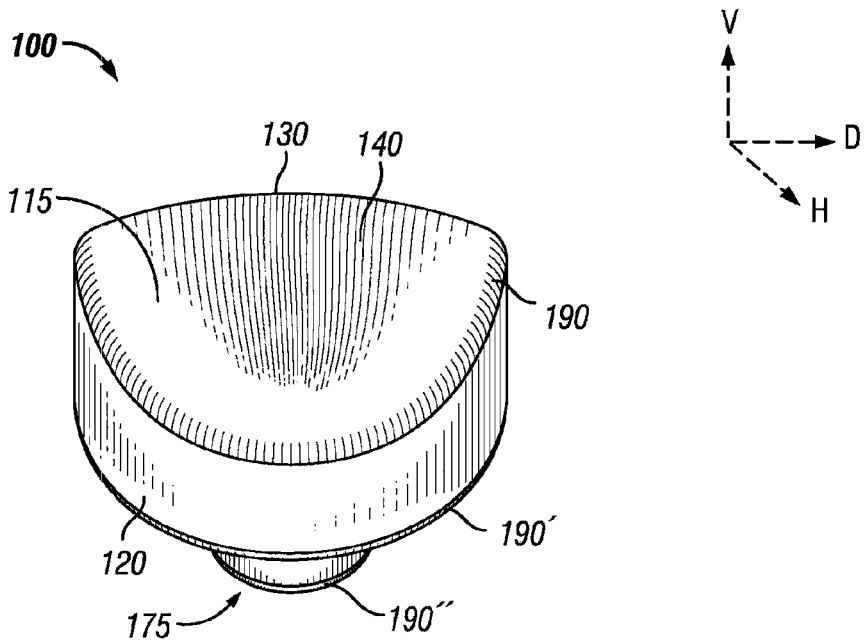
FIG. 4 is a medial side view of the implant of FIG. 1.
Figure 5:
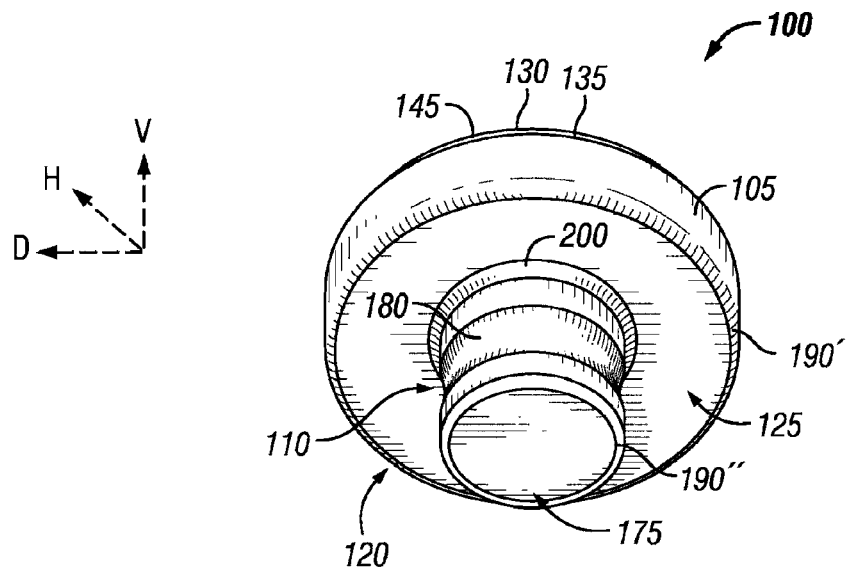
FIG. 5 is a lateral side view of the implant of FIG. 1.
Figure 6:
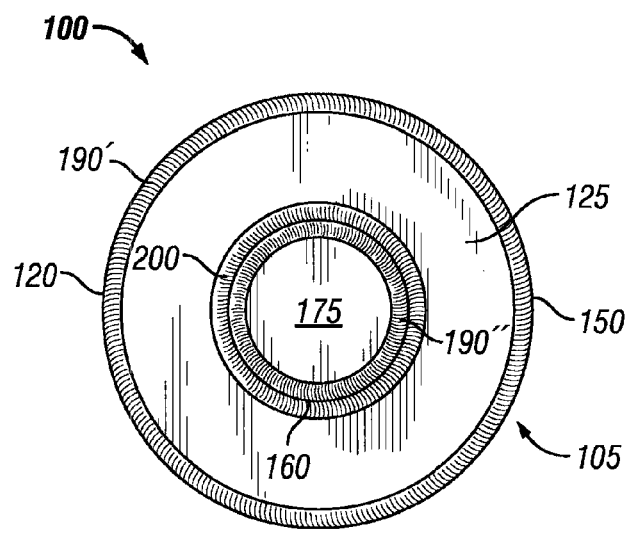
FIG. 6 is a bottom view of the implant of FIG. 1.
Figure 7:
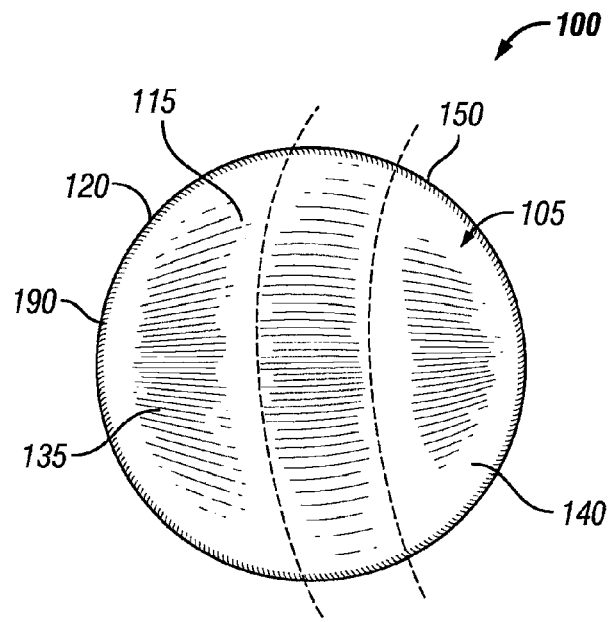
FIG. 7 is a top view of the implant of FIG. 1.

With reference to FIGS. 2 and 3, the stem 110 may extend from the lower surface 125 of the head 105 in a general direction away from the upper surface 115. Preferably, the head 105 and stem 110 are formed as a non-modular, unibody, i.e., one integral piece without intervening mechanical connection. In this manner, the stem 110 may extend in a direction parallel to the normal to the lower surface 125 of the head 105.

The stem 110 may be of a single cylindrical or a single, truncated conical shape. Alternatively, the stem 110 may be of a generally cylindrical shape having one or more circumferential grooves 180 about the perimeter of the stem 110. The lower surface 125 of the head 105 may blend into the cylindrical portion 150 of the stem 110 with a corner fillet 200. The corner fillet 200 may have a radius of about 1.5 millimeters.

The shape of the circumferential groove(s) 180 may be defined by a partial torus having a tubular radius ranging from about 0.25 millimeters to about 2 millimeters, alternatively from about 0.5 millimeters to about 1 millimeter, alternatively about 1 millimeter. In embodiments having more than one circumferential groove 180 (not shown), each circumferential groove may be spaced apart from respective groove at a distance ranging from about 1 millimeter to about 3 millimeters from each other, alternatively from about 2 millimeters to about 2.5 millimeters from each other along the central axis of the stem 110. In an embodiment, the circumferential groove 180 may be located at the center of the length of the stem 110. In an embodiment, the circumferential groove 180 may be about 0.5 millimeters deep into the stem 110. The circumferential groove 180 may blend into the stem 110 with blends having edge radii of from about 0.1 millimeters to about 1 millimeters, alternatively about 0.8 millimeters.

The implant 100 many be manufactured from a variety of suitable materials, having the requisite strength and biocompatibility characteristics to function as an implant, including but not limited to any of the following, individually or in combination, graphite, pyrocarbon, ceramic, aluminum oxide, silicone nitride, silicone carbide or zirconium oxide; metal and metal alloys, e.g., Co—Cr—W—Ni, Co—Cr—Mo, CoCr alloys, CoCr molybdenum alloys, Cr—Ni—Mn alloys; powder metal alloys, 316L or other stainless steels, Ti and Ti alloys including Ti 6A1-4V ELI; polymers, e.g., polyurethane, polyethylene, polypropylene, thermoplastic elastomers, polyaryletherketones such as polyetherehterketone (PEEK) or polyetherketoneketone (PEKK); biomaterials such as polycaprolactone; and diffusion hardened materials such as Ti-13-13, zirconium and niobium. Moreover, the implant 100 may be coated with a variety of suitable materials, including any of the following, individually or in combination, porous coating systems on bone-contacting surfaces, hydrophilic coatings on load-bearing surfaces, hydroxyapatite coatings on bone-contacting surfaces, and tri-calcium phosphate on bone-contacting surfaces. Other suitable coatings include growth factors and other biological agents such as bone morphogenetic proteins (BMP's), transforming growth factor beta, among others. Additionally, components of the invention may be molded or cast, hand-fabricated or machined.

In an illustrative embodiment, the implant 100 may be composed of graphite and pyrocarbon. Preferably, the implant 100 is graphite and includes a coating of pyrocarbon. The pyrocarbon coating may have an average thickness of from about 100 to about 1000 microns, alternatively from about 200 microns to about 500 microns, alternatively from about 250 to about 500 microns, alternatively about 350 microns. The pyrocarbon coating may have an elastic modulus from about 15 gigapascals ("GPa") to about 22 GPa, alternatively about 20 GPa. The pyrocarbon coating may further have a strength of at least 200 megapascals ("MPa"), alternatively at least about 300 MPa, alternatively at least about 400 MPa. The pyrocarbon elastic modulus and strength are preferably tested using four-point bend, third-point-loading substrated specimens of dimensions 25 millimeters by 6 millimeters by 0.4 millimeters. Preferably the pyrocarbon is pyrolytic carbon as described in *Pure Pyrolytic Carbon: Preparation and Properties of a New Material, On-X Carbon for Mechanical Heart Valve Prostheses*, Ely et al, J. Heart Valve Dis., Vol. 7, No. 6, A00534 (November 1998), alternatively pyrocarbon is pyrolytic carbon as described in the before-mentioned J. Heart Valve Dis. publication, but includes additional silicon.

In certain embodiments, the upper surface 115 and the contiguous edge blends, i.e., the blends of the upper surface into the perimeter surface, are polished.

The above-described implants may be used to repair damaged articular cartilage in humans, including ankles, knees, wrists, elbows, shoulders, and the like joints. In another illustrative embodiment or a preferred method, a patient having articular cartilage damage may be identified. The patient may be fully informed of the risks associated of surgery, and consents to the same. An incision may be made near the damaged articular cartilage. The lesion to be repaired may be identified, and an implant having dimensions compatible with the lesion may be selected. The implant may be slightly smaller or slightly larger than the lesion. In various embodiment, the implant may be from about 0.1 percent to about 20 percent smaller or larger than the lesion. A hole may be then formed, i.e., drilled, punched, or broached, through the cartilage and the subchondral bone into the cancellous bone. The dimensions of the hole may be slightly less than the diameter and length dimensions of the stem and head of the implant. This may be achieved, for example, by using a drill bit or reamer and then a counterbore bit. The minimum length of the hole may be equal to or slightly greater than the length of the stem 110 of the implant 100, along the central axis of the stem. An amount of healthy and damaged cartilage may be removed near the lesion so that the lower surface 125 and at least a portion of the perimeter surface 120 of the head 105 may rest against the patient's bone. It may be preferable to remove as little healthy cartilage as possible. The stem 110 of the implant 100 may be inserted into the hole, and the lower surface 125 and at least a portion of the perimeter surface 120 of the implant's 100 head 105 may rest against the bone. The incision may be then sutured by any of several known methods. In an embodiment and without wishing to be bound by the theory, Applicant believes that the stem of the implant may be secured into the prepared hole by a friction fit and over time human bone may grow into the circumferential groove.

While specific alternatives to steps of the specific embodiments have been described herein, additional alternatives not specifically disclosed but known in the art are intended to fall within the scope of the present implants and methods thereof. For example, while specific dimensions, and ranges of dimensions, have been provided further dimensions may reasonably fall within the scope of the present implant and methods thereof. Thus, it is understood that other applications of the present disclosure will be apparent to those skilled in the art upon reading the descriptions of the described illustrative embodiments and after consideration of the appended claims and drawing figures.

The invention claimed is:

1. An implant comprising:
   (a) a head having an upper surface, a perimeter surface, and a lower surface, wherein:
      (i) the upper surface blends into the perimeter surface and the perimeter surface blends into the lower surface;
      (ii) the upper surface has a general shape of at least a portion of a superior articular surface of a talus and at least a portion of a medial articular surface of a talus;
      (iii) the upper surface includes a convex first portion having a general shape of a portion of a toroid, a convex-concave second portion having a general saddle shape of a convex-concave portion of a toroid, and a third portion having a general shape of a portion of a surface of a right circular cone having an aperture angle ranging from about 120 degrees to about 178 degrees, wherein the first portion is tangent on its lateral edge to the medial edge of the second portion and the first portion is tangent on its medial edge to the lateral edge of the third portion; wherein the toroid of the convex first portion has a major radius ranging from about 9 millimeters to about 31 millimeters, and a minor tubular radius ranging from about 2 millimeters to about 6 millimeters; and
   (b) a stem extending away from the lower surface, wherein:
      (i) the stem has at least one circular perimeter along an axis normal to the lower surface, and a maximum stem circular perimeter at the intersection of the stem and the lower surface,
      (ii) the maximum stem circular perimeter is less than a maximum diameter of the head perimeter surface,
      (iii) the stem has a cylindrical portion.

2. The implant of claim 1, wherein the cylindrical portion of the stem extends at least one millimeter from the lower surface along a direction parallel to the lower surface normal; and wherein the stem has at least one circumferential groove, wherein the at least one circumferential groove extends continuously around the at least one circular perimeter, wherein the at least one circumferential groove is defined between two adjacent circular perimeters and has the shape of a partial torus extending radially inward of the adjacent circular perimeters, wherein the at least one circumferential groove blends into at least one of the two adjacent circular perimeters, wherein the stem blends into the lower surface.

3. The implant of claim 1, wherein the toroid of the convex-concave second portion has a major radius in a plane of convex curvature ranging from about 20 millimeters to about 100 millimeters, and a minor tubular radius in a plane of concave curvature ranging from about 10 millimeters to about 70 millimeters.

4. The implant of claim 1, wherein an apex point is present on the upper surface first portion.

5. The implant of claim 4, wherein the stem extends away from the lower surface of the head in a direction away from the upper surface and in a direction parallel to the lower surface normal.

6. The implant of claim 1, wherein an apex point is present on the upper surface first portion.

7. The implant of claim 1, wherein the stem extends away from the lower surface of the head in a direction away from the upper surface and in a direction parallel to the lower surface normal wherein the lower surface is generally flat and planar.

8. The implant of claim 1, wherein the cylindrical portion has a diameter ranging from about 2 millimeters to about 10 millimeters, and an overall length ranging from about 0.1 millimeters to about 10 millimeters.

9. The implant of claim 1, wherein the lower surface of the head blends into the cylindrical portion of the stem with a corner fillet, the corner fillet having a radius from about 0.1 millimeters to about 3 millimeters.

10. The implant of claim 9, wherein the circumferential grooves blend into the stem and has an edge radius ranging from about 0.1 millimeters to about 1 millimeters.

11. The implant of claim 1, wherein the head and the stem each consist essentially of: a graphite core and a pyrocarbon coating, the pyrocarbon coating having an average thickness ranging from about 100 to about 1000 microns.

12. The implant of claim 11, wherein the pyrocarbon coating has an elastic modulus ranging from about 15 GPa to about 22 GPa.

13. The implant of claim 12, wherein the pyrocarbon coating has an elastic modulus of about 20 GPa and a strength of at least 400 MPa.

14. The implant of claim 13, wherein the upper surface and contiguous edge blends are polished, and the lower surface and stem are coated with hydroxyapatite.

15. The implant of claim 1, wherein the convex first portion, the convex-concave second portion, and the third portion are not in the same plane as the perimeter surface.

16. The implant of claim 1, wherein the perimeter surface is generally cylindrical.

17. The implant of claim 1, wherein the blend of the upper surface into the perimeter surface and the blend of the perimeter surface into the lower surface independently have an edge radius ranging from about 0.1 mm to about 1 mm.

18. A method of repairing articular cartilage comprising:
(A) locating articular cartilage having a lesion;
(B) utilizing an implant having dimensions compatible with the lesion, wherein the implant comprises;
  (a) a head having an upper surface, a perimeter surface, and a lower surface, wherein:
    (i) the upper surface blends into the perimeter surface and the perimeter surface blends into the lower surface;
    (ii) the upper surface has a general shape of at least a portion of a superior articular surface of a talus and at least a portion of a medial articular surface of a talus;
    (iii) the upper surface includes a convex first portion having a general shape of a portion of a toroid, a convex-concave second portion having a general saddle shape of a convex-concave portion of a toroid, and a third portion having; a general shape of a portion of a surface of a right circular cone having an aperture angle ranging from about 120 degrees to about 178 degrees, wherein the first portion is tangent on its lateral edge to the medial edge of the second portion and the first portion is tangent on its medial edge to the lateral edge of the third portion; wherein the toroid of the convex first portion has a major radius ranging from about 9 millimeters to about 31 millimeters, and a minor tubular radius ranging from about 2 millimeters to about 6 millimeters; and
  (b) a stem extending away from the lower surface, wherein:
    (i) the stem has at least one circular perimeter along an axis normal to the lower surface. and a maximum stem circular perimeter at the intersection of the stem and the lower surface,
    (ii) the maximum stem circular perimeter is less than a maximum diameter of the head perimeter surface,
    (iii) the stem has a cylindrical portion;
(C) forming a cavity in the articular cartilage, subchondral bone, and cancellous bone; and
(D) engaging the implant with the cavity so that the lower surface, at least a portion of the perimeter surface abut against the subchondral and cancellous bone and the stein abuts against the cancellous bone.

19. The method of claim 18, wherein forming the cavity includes placement of autograft, allograft bone, or various bone graft substitute material into the lesion.

20. The method of claim 18, wherein the cylindrical portion of the stem extends at least one millimeter from the lower surface along a direction parallel to the lower surface normal; and wherein the stem has at least one circumferential groove, wherein the at least one circumferential groove extends continuously around at least one of the plurality of circular perimeters, wherein the at least one circumferential groove is defined between two adjacent circular perimeters and has the shape of a partial torus extending radially inward of the adjacent circular perimeters, wherein the at least one circumferential groove blends into at least one of the two adjacent circular perimeters, wherein the stem blends into the lower surface.

* * * * *